(12) United States Patent
Freeman

(10) Patent No.: US 8,025,626 B2  
(45) Date of Patent: Sep. 27, 2011

(54) BIOPSY FORCEPS WITH HOLD OPEN JAW FEATURE

(76) Inventor: Ken Freeman, Laconia, NH (US)

( * ) Notice: Subject to any disclaimer, the term of this patent is extended or adjusted under 35 U.S.C. 154(b) by 165 days.

(21) Appl. No.: 12/328,031

(22) Filed: Dec. 4, 2008

(65) Prior Publication Data

US 2009/0287112 A1   Nov. 19, 2009

Related U.S. Application Data

(60) Provisional application No. 61/052,817, filed on May 13, 2008.

(51) Int. Cl.  
*A61B 10/00* (2006.01)

(52) U.S. Cl. .......... 600/567; 600/564; 600/562

(58) Field of Classification Search .......... 600/562–584; 606/167  
See application file for complete search history.

(56) References Cited

U.S. PATENT DOCUMENTS

| 4,763,668 | A | * | 8/1988 | Macek et al. ............ 600/564 |
| 5,715,832 | A | * | 2/1998 | Koblish et al. .......... 600/564 |
| 5,840,044 | A | * | 11/1998 | Dassa et al. ............ 600/567 |
| 5,971,940 | A | * | 10/1999 | Baker et al. ............ 600/567 |
| 7,775,989 | B2 | * | 8/2010 | Nakao .................... 600/564 |
| 2005/0049520 | A1 | * | 3/2005 | Nakao .................... 600/562 |

* cited by examiner

*Primary Examiner* — Jeffrey G Hoekstra  
(74) *Attorney, Agent, or Firm* — Bourque and Associates, PA

(57) ABSTRACT

Biopsy forceps have a handle located at the proximal end and an end jaw assembly located at the distal end. The handle and jaw assembly are connected by a flexible catheter tube. The handle includes a body portion and an actuator portion that controls the jaw assembly. The actuator is axially displaced relative to the handle body to open and close the pair of opposed jaws. The jaw assembly consists of a housing composed of a first and second portion, which holds the pair of opposed jaws and a distal actuator. The distal actuator is controlled by the handle actuator which controls the jaws positioning. A locking mechanism is attached to the handle actuator and can lock the jaws in an open position. To close the jaws, the locking mechanism can be pushed to its unlocked position and the actuator slid to its back position.

11 Claims, 4 Drawing Sheets

BIOPSY FORCEPS WITH HOLD OPEN JAW FEATURE

CROSS-REFERENCE TO RELATED APPLICATIONS

This application is related to and claims priority from U.S. Provisional Application No. 61/052,817 filed on May 13, 2008 entitled Biopsy Forceps With Hold Open Jaw Feature, which is incorporated fully herein by reference.

TECHNICAL FIELD

The present invention relates to disposable biopsy forceps and more particularly, relates to an improved biopsy forceps device with a hold open jaw feature including a spring loaded locking nosepiece.

BACKGROUND INFORMATION

Biopsy forceps are used to obtain tissue samples from a particular site in a patient's body for analysis. Such samples can be taken from the heart, stomach, lungs and the like. Typical biopsy forceps include a long flexible catheter tube having a pair of opposed jaws at a distal end and a handle with an actuator at the proximal end. The physician can manipulate the actuator to open and close the jaws.

In order to take a tissue sample from a patient, the physician must insert the catheter tube into a guide sheath which has been inserted into one of the patient's vessels. Next, the distal end of the biopsy forceps is inserted into the guide sheath, which then guides it into the patient's vessel. From the patient's vessel the physician can direct the catheter tube to the site the physician wishes to biopsy. Once the catheter tube is directed to the biopsy site, the physician can control the jaws using the handle, which remains outside the patient's body. By using a trigger located on the handle, the physician can open and close the jaws of the device in order to take a tissue sample. Once the tissue sample has been taken, the physician must keep the jaws in a closed position to remove the sample from the patient's body. Once the sample has been removed from the patient's body, it can be removed from the forceps and examined.

Multiple handle assemblies have been used to maneuver the catheter tube and jaw assembly into the proper position to perform the biopsy. The first biopsy forceps did not contain a locking mechanism to keep the jaws opened while the physician removes the biopsy sample. Therefore, the physician had to hold the jaws open while positioning the jaw assembly for tissue removal, which often required the use of two hands or another person.

Other biopsy forceps contain a locking mechanism to lock the forceps in a closed position. By locking the forceps in a closed position the physician is able to ensure that the jaws do not cut the patient's vessel as the catheter tube travels to the biopsy site and also ensures that the tissue sample remains in the jaws once the sample is taken.

Later biopsy forceps locking mechanisms are used to lock the forceps in an open position. By locking the biopsy forceps in an open position, the physician is able to position the jaws for tissue sample removal without having to hold the biopsy forceps in the open position. In addition, these biopsy forceps remain in a closed position while unlocked to enable the physician to more easily move the catheter tube through the patient's vessel and to remove the tissue sample from the patient's body. These biopsy forceps also allow the physician to remove the tissue sample from the jaws without the aid of another person to hold the jaws in the open position. However, these locking mechanisms are incorporated into the handle body, which can result in the forceps lock slipping and the jaws closing before the physician wants them to.

Accordingly, what is needed is a locking mechanism, which is not incorporated with the handle body. By having the locking mechanism incorporated with the handle body the potential for the physician to accidentally release the lock while positioning the jaws at the biopsy site increases. Also what is needed is a locking mechanism which is easier for the physician to control.

SUMMARY

The present invention features a new locking mechanism for biopsy forceps. The new locking mechanism contains a spring loaded locking nosepiece attached to the handle of the biopsy forceps. The biopsy forceps of the present invention contains a proximal and distal end. At the proximal end there is a handle composed of a handle body and actuator, which axially displace relative to each other. At the distal end there is a jaw assembly composed of a pair of jaws and a jaw housing, which holds and controls the jaws.

The handle at the proximate end and the jaw assembly at the distal end are connected by a catheter tube. The catheter tube contains the means for controlling the jaw assembly with the handle. By axially moving the actuator forward on the handle body the jaws on the distal end move from a closed to an open position.

Once the actuator has been moved forward, the locking mechanism can be used. The nosepiece can be pushed into place to lock the biopsy forceps jaws in an open position. The nosepiece locks and remains in place because of the force exerted on the handle body by the spring located inside the actuator portion of the handle. Once the physician is ready to remove the tissue sample, the actuator is moved forward and the locking mechanism can be used. Releasing the nosepiece allows the jaws to close, allowing for reinsertion into the patients body for any additional samples required.

It is important to note that the present invention is not intended to be limited to a system or method, which must satisfy one or more of any stated objects or features of the invention. It is also important to note that the present invention is not limited to the preferred, exemplary, or primary embodiment(s) described herein. Modifications and substitutions by one of ordinary skill in the art are considered to be within the scope of the present invention.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
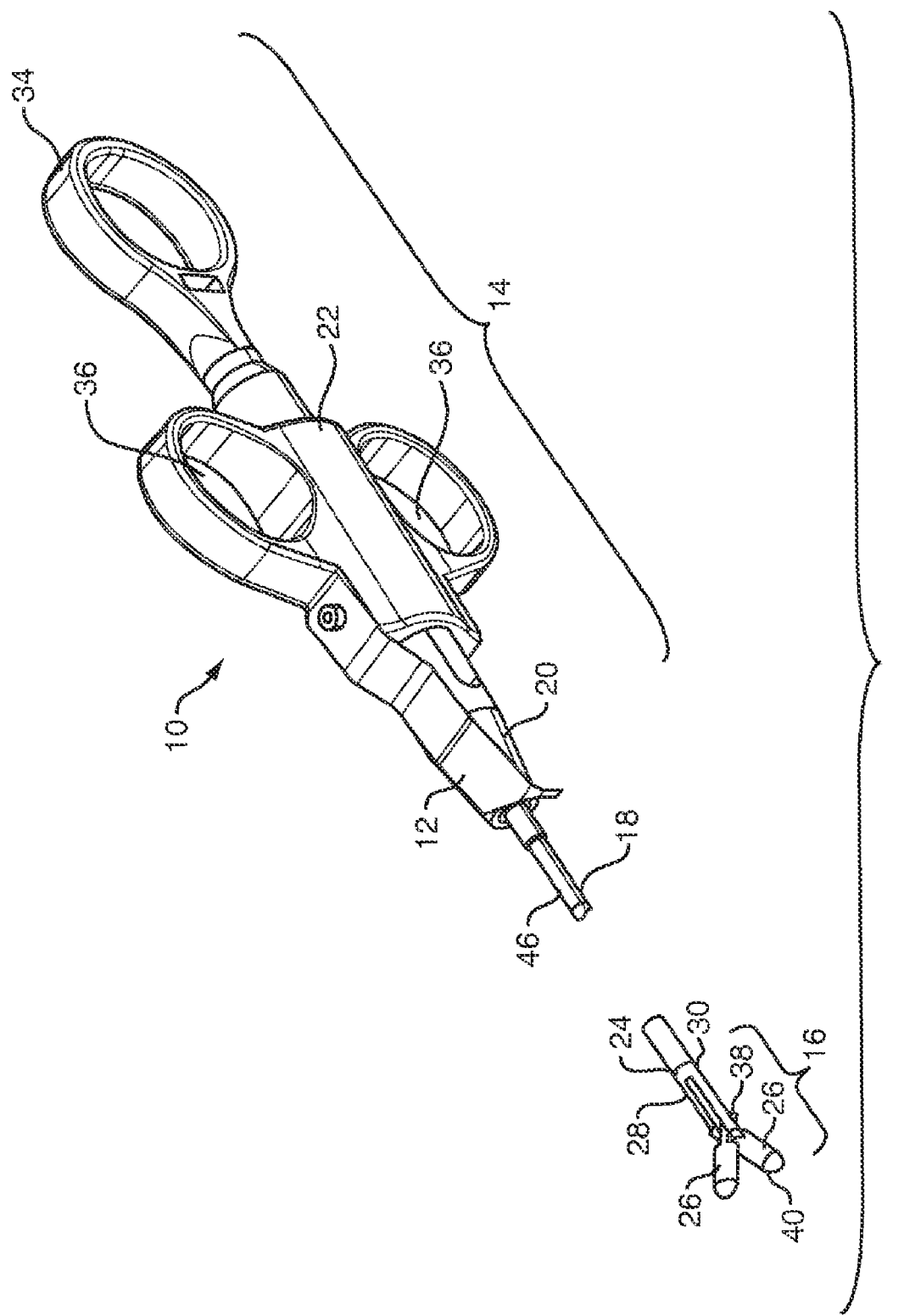
FIG. 1 is a perspective view of the biopsy forceps according to the present invention in the locked position with open jaws.
Figure 2:
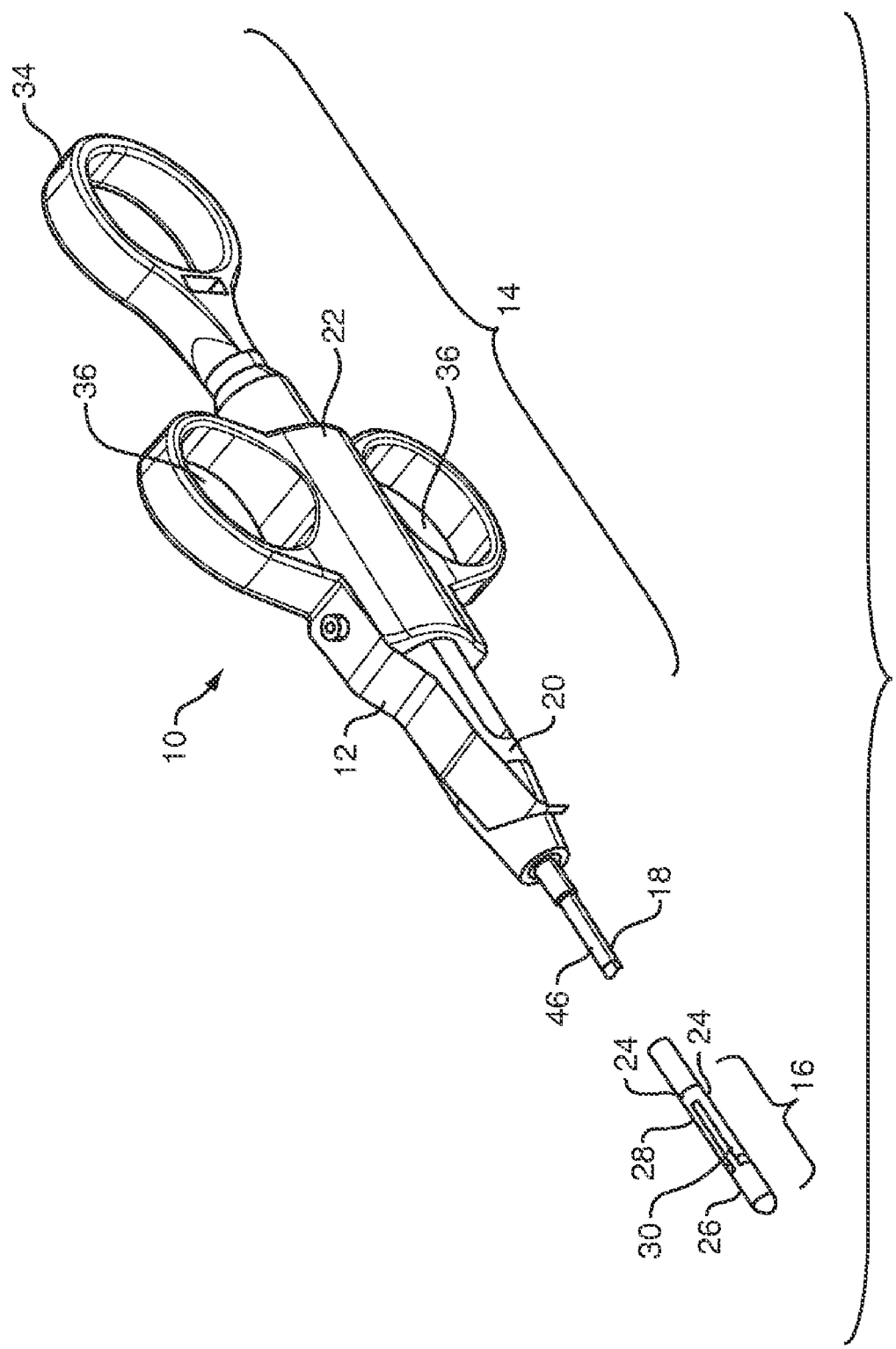
FIG. 2 is a perspective view of the biopsy forceps according to the present invention in the unlocked position with closed jaws.
Figure 3:
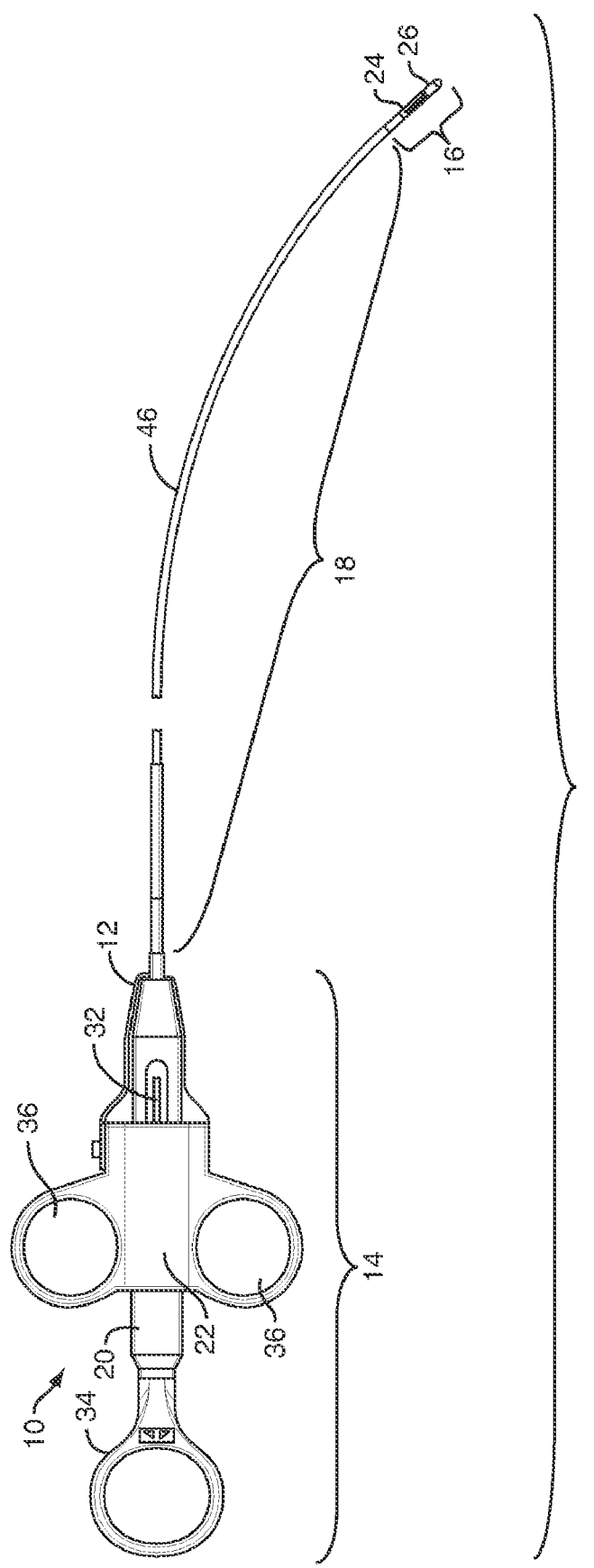
FIG. 3 is a side view of the biopsy forceps according to the present invention in a locked position.
Figure 5:
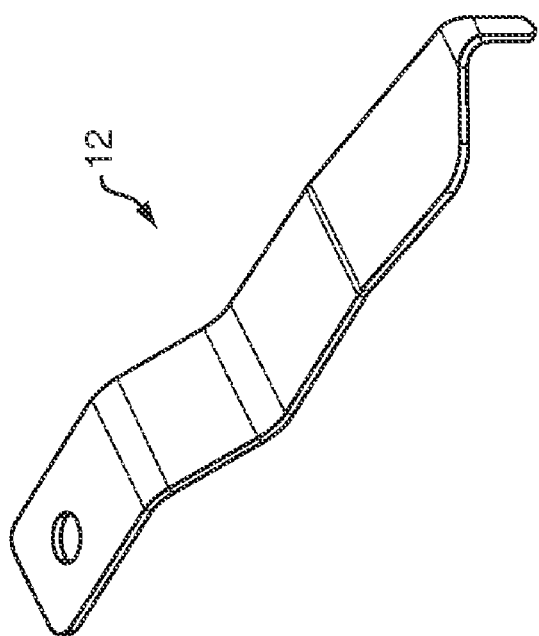
FIG. 5 is a perspective view of the locking mechanism of the biopsy forceps according to the present invention.
Figure 4:
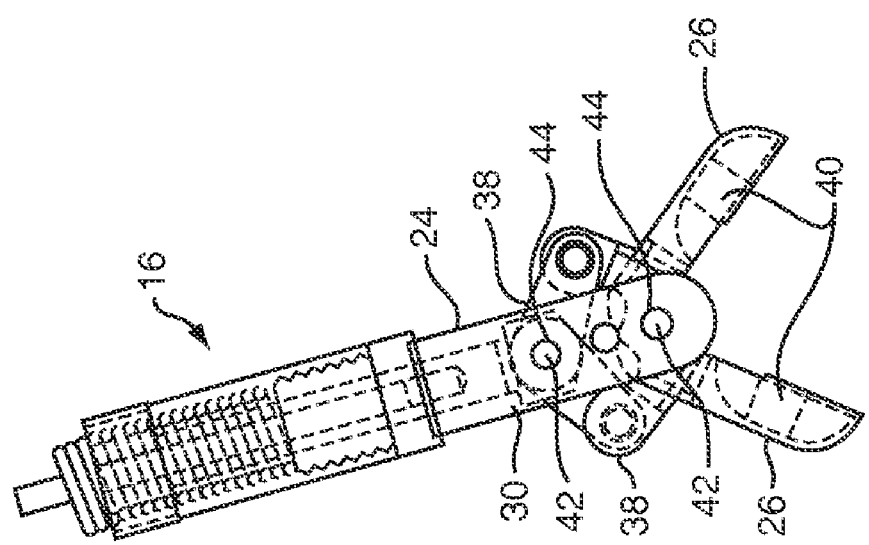
FIG. 4 is a see-through side view of the end jaw assembly of the biopsy forceps that can be utilized with the present invention.

The present invention is directed to biopsy forceps 10, FIG. 1, with an improved locking mechanism 12. The biopsy forceps 10 are composed of a handle 14 and an end jaw assembly 16 connected by a flexible catheter tube 18. Handle 14 is composed of a body portion 20 and an actuator portion 22. Body portion 20 and actuator 22 are axially displaceable relative to each other. End jaw assembly 16 contains a housing 24 and a pair of opposed jaws 26. Housing 24 contains a first portion 28 and a second portion 30, which holds jaws 26 to jaw assembly 16.

Body portion 20 contains a spring 32 inside of body portion 20 and a thumb ring 34 at the proximal end of body portion 20. Spring 32 enables the spring loaded locking mechanism 12 to operate and keeps jaws 26 in an open position by exerting a force onto actuator 22 when locking mechanism 12 is in a locked position. Actuator 22 contains two finger holes 36 at the proximal end of actuator 22 and an attachment means for the locking mechanism 12 at the distal end of actuator 22. To operate biopsy forceps 10 a user places their thumb into thumb ring 34 and two other fingers into finger holes 36 enabling them to slide the actuator 22 into a locked or unlocked position.

The housing 24 of end jaw assembly 16 contains a pair of opposed jaws 26 and a distal actuator 38. The first and second portions, 28 and 30, of housing 24 contain slots 44 to hold pins 42 into place. Pins 42 secure jaws 26 within end jaw assembly 16. Distal actuator 38 enables jaws 26 to move to open and closed positions to take a tissue sample. The tissue sample is held within the inner cups 40 of jaws 26 to allow the physician to remove it from the patient's body.

Handle 14 and end jaw assembly 16 are connected by catheter tube 18. Catheter tube 18 contains a tube inner member, not shown, and a tube outer member 46 as is well known in the art. The inner member contains the means for connecting actuator 22 to distal actuator 38 to enable the movements of actuator 22 to control distal actuator 38. Outer member 46 protects the control means located within the inner member of catheter tube 18, while catheter tube 18 travels through a patient's vessel.

The preferred method of operation of biopsy forceps 10 is for the physician to place his thumb into thumb ring 34 and two other fingers into finger holes 36 after the patient has been prepared for the biopsy. Then the physician should guide catheter tube 18 into the patient's vessel, jaw assembly 16 first, while locking mechanism 12 is in an unlocked position and jaws 26 are in a closed position. Once the physician has maneuvered jaws 26 to the biopsy site, the physician can slide actuator 22 distally on handle body 20 to open jaws 26. In the open position jaws 26 open to a minimum of 80 degrees to ensure an ample sample can be taken to decrease the need for taking multiple samples. With jaws 26 in an open position the physician can maneuver them into position to take the tissue sample. Once jaws 26 are in the proper position to take a tissue sample, the physician can slide actuator 22 proximally on handle body to close jaws 26. As jaws 26 close their sharp edges slice through the patient's tissue and leave a tissue sample inside cups 40 of jaws 26. Now the physician can remove catheter tube 18 and jaw assembly 16 from the patient's vessel. After a tissue sample has been taken the physician can secure locking mechanism 12 into locked position to remove the tissue sample from cups 40. This locking mechanism 12 enables the physician to remove the tissue sample more easily and quickly because it does not require the aid of another person.

Modifications and substitutions by one of ordinary skill in the art are considered to be within the scope of the present invention, which is not to be limited except by the following claims. As mentioned above, the present invention is not intended to be limited to a system or method which must satisfy one or more of any stated or implied objectives or features of the invention and should not be limited to the preferred, exemplary, or primary embodiment(s) described herein. The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention which is not to be limited except by the allowed claims and their legal equivalents.

The invention claimed is:

1. A jaw assembly hold open locking device for biopsy forceps device comprising:
    a flexible catheter tube having a proximal end and a distal end;
    a handle disposed at said proximal end of said flexible catheter tube, said handle including a body portion and an actuator portion axially displaceable along a longitudinal direction relative to said body portion;
    an end jaw assembly disposed at said distal end of said flexible catheter tube, said end jaw assembly including a pair of opposed end jaws operable between an open position and a closed position, said pair of opposed end jaws pivotable about an axis that is fixed without any translational movement along said longitudinal direction; and
    a locking mechanism disposed on an exterior surface of said handle, said locking mechanism having a first end pivotably fixed to said actuator portion on said exterior surface of said handle and a second end configured for moving in and out of engagement with an end region of said body portion on said exterior surface of said handle, when in engagement with said end region of said body portion of said exterior surface of said handle for locking said jaw assembly in said open position to facilitate the removing of the biopsy sample, and when disengaged from said end region of said body portion of said exterior surface of said handle, for allowing said jaw assembly to return to said closed position.

2. The biopsy forceps of claim 1, wherein said body portion and said actuator are axially locked relative to one another when said jaw assembly is locked in said open position.

3. The biopsy forceps of claim 2, further including an attachment means configured to secure said locking mechanism to said handle.

4. The biopsy forceps of claim 2, wherein said handle includes a spring for sliding said actuator portion in a position corresponding to said open position of said jaws.

5. The biopsy forceps of claim 1, wherein said catheter tube includes an inner member and an outer member axially movable with respect to said inner member, said inner member being connected to said actuator and a distal actuator.

6. The biopsy forceps of claim 1, wherein said pair of opposed end jaws each include a cup having a sharp edge.

7. The biopsy forceps of claim 1, wherein said jaw assembly includes a housing having a first portion coupled to a second portion for containing said jaws.

8. The biopsy forceps of claim 7, wherein said first portion includes pins for securing said jaws in holes of said jaw assembly.

9. The biopsy forceps of claim 7, wherein said jaw assembly includes a distal actuator connected to a distal end of said catheter tube and operably connected to said jaws.

10. The biopsy forceps of claim 1, wherein said pair of opposed end jaws open to a minimum of 80 degrees.

11. A biopsy forceps device comprising:
- a flexible catheter tube having a proximal end and a distal end;
- a handle disposed at said proximal end of said flexible catheter tube, said handle including a body portion and an actuator portion axially displaceable relative to said body portion;
- an end jaw assembly disposed at said distal end of said flexible catheter tube, said end jaw assembly including a pair of opposed end jaws operable between an open position and a closed position; and
- a locking mechanism disposed on an exterior surface of said handle, said locking mechanism having a first end pivotably fixed to said actuator portion on said exterior surface of said handle and a second end configured for moving in and out of engagement with an end region of said body portion on said exterior surface of said handle, when in engagement with said end region of said body portion of said exterior surface of said handle for locking said jaw assembly in said open position to facilitate the removing of the biopsy sample, and when disengaged from said end region of said body portion of said exterior surface of said handle, for allowing said jaw assembly to return to said closed position.

* * * * *